US012406597B2

(12) United States Patent
Alexander, Jr. et al.

(10) Patent No.: US 12,406,597 B2
(45) Date of Patent: Sep. 2, 2025

(54) REAL-TISSUE HEAD AND NECK SURGICAL TRAINING SYSTEM AND ASSOCIATED METHODS

(71) Applicant: INTUITIVE SURGICAL OPERATIONS, INC., Sunnyvale, CA (US)

(72) Inventors: John C. Alexander, Jr., Pinehurst, NC (US); Richard H. Feins, Chapel Hill, NC (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 549 days.

(21) Appl. No.: 17/808,132

(22) Filed: Jun. 22, 2022

(65) Prior Publication Data

US 2023/0017321 A1  Jan. 19, 2023

Related U.S. Application Data

(60) Provisional application No. 63/221,973, filed on Jul. 15, 2021.

(51) Int. Cl.
G09B 23/30 (2006.01)
C12N 5/071 (2010.01)
G09B 23/34 (2006.01)

(52) U.S. Cl.
CPC ......... *G09B 23/306* (2013.01); *C12N 5/0697* (2013.01); *G09B 23/303* (2013.01); *G09B 23/34* (2013.01)

(58) Field of Classification Search
CPC ...... G09B 23/28; G09B 23/30; G09B 23/306; G09B 23/32; G09B 23/34
See application file for complete search history.

(56) References Cited

U.S. PATENT DOCUMENTS

| 5,358,408 | A  | * | 10/1994 | Medina ................. G09B 23/28 434/262 |
| 8,647,124 | B2 |   | 2/2014  | Bardsley et al. |
| 8,852,208 | B2 |   | 10/2014 | Gomez et al. |
| 9,295,524 | B2 |   | 3/2016  | Schena et al. |
| 9,358,074 | B2 |   | 6/2016  | Schena et al. |
| 10,679,520 | B2 | * | 6/2020 | Hofstetter .............. G09B 23/30 |
| 2017/0076636 | A1 | * | 3/2017 | Moore ................. G09B 23/285 |
| 2020/0286406 | A1 | * | 9/2020 | Alexander ............. A61B 34/10 |

(Continued)

FOREIGN PATENT DOCUMENTS

WO  WO-2019246525 A1  12/2019

OTHER PUBLICATIONS

Avraham, M., "Training Platform for Transoral Robotic Surgery," Tech ID: 31807, UCLA—Technology Development Group, 2018, 1 page.

(Continued)

*Primary Examiner* — Kurt Fernstrom
(74) *Attorney, Agent, or Firm* — ALLEN, DYER, DOPPELT, + GILCHRIST, P.A.

(57) ABSTRACT

A real-tissue surgical training system includes a base and a harvested porcine tissue cassette. A substrate is configured to be removably mounted to the base. Harvested porcine tissue is carried by the substrate and configured to simulate the oropharynx region of the human body and to receive a surgical tool therein for surgical training.

21 Claims, 12 Drawing Sheets

(56) References Cited

U.S. PATENT DOCUMENTS

2021/0043114 A1* 2/2021 Alexander ............. G09B 23/34
2022/0101756 A1* 3/2022 Drew ................... G09B 23/285

OTHER PUBLICATIONS

Geoghegan, R., et al., "Development of a Transoral Robotic Surgery Training Platform," Annual International Conference of the IEEE Engineering in Medicine and Biology Society, Jul. 2019, pp. 5851-5854.
Mendelsohn, A.H., et al., "Transoral Robotic Surgical Proficiency Via Real-Time Tactile Collision Awareness System," Laryngoscope, Dec. 2020, vol. 130 (Suppl 6): S1-S17.
Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

REAL-TISSUE HEAD AND NECK SURGICAL TRAINING SYSTEM AND ASSOCIATED METHODS

PRIORITY APPLICATION(S)

This utility application is based upon U.S. provisional patent application Ser. No. 63/221,973 filed Jul. 15, 2021, the disclosure which is hereby incorporated by reference in its entirety.

FIELD OF THE INVENTION

Aspects of the present disclosure relate to surgical training, and more particularly, to a real-tissue surgical training system that simulates the head and neck of the human body, including the oropharynx, and related methods.

BACKGROUND OF THE INVENTION

Operating in the throat of the human body, such as in the pharynx and/or larynx, requires precise surgical skill to manipulate surgical tools, imaging devices, and other surgical instruments within confined spaces that are inaccessible to human hands absent open surgery. Surgeons may use manual laparoscopic and/or robotically controlled surgical tools to perform diagnostic procedures, remove tumors, and perform other surgical procedures within those recessed areas of the pharynx and larynx using minimally invasive medical techniques without the need for open surgery.

Minimally invasive medical techniques are intended to reduce the amount of tissue that is damaged during diagnostic or surgical procedures, thereby reducing patient recovery time, discomfort, and harmful side effects. Such minimally invasive techniques may be performed through one or more surgical incisions or through natural orifices in a patient anatomy. Through these incisions or natural orifices, clinicians may insert minimally invasive medical instruments (including surgical, diagnostic, therapeutic, or biopsy instruments) to reach a target tissue location. Minimally invasive robotically-assisted and computer-assisted medical systems have been developed to increase a surgeon's dexterity and avoid some of the limitations on traditional minimally invasive techniques.

Recently, greater numbers of surgeons have relied on minimally invasive transoral robotic surgery (TORS) as a preferred surgical technique to operate on the oropharynx region of the human body. In TORS procedures, robotic or computer controlled instruments are inserted into a patient's mouth and are navigated down to the areas of interest. The surgeon uses some form of remote control, e.g., a servomechanism, or the like, to manipulate movement of the robotic or computer controlled instruments. The robotic or computer controlled instruments may be coupled to one or more manipulators that include two or more links coupled together by one or more actively and/or passively controlled joints. While viewing typically a three-dimensional image of the surgical site on a suitable viewer or display, the surgeon performs procedures on the patient by manipulating control input devices, which in turn control the motion of the robotic or computer controlled instruments via the manipulators.

The surgical skills required to operate in the confined spaces of the oropharynx region of the human body mandates many years of surgical training and experience to acquire the surgical skill necessary to reduce collateral damage to surrounding tissues. The technical challenges of operating in the throat by TORS or manual laparoscopic techniques makes surgical training and proficiency in these techniques advantageous to avoid unwanted anatomic collisions. This surgical experience is difficult to acquire without extensive training under the guidance of a skilled surgeon over many years.

Various techniques have been developed to train surgeons in TORS and similar laparoscopic techniques. For example, a live pig has been used for training surgeons since the oropharynx region of a pig is similar to the oropharynx region of the human body. Surgically training on a live pig simulates surgical training in the oropharynx region of the human body because manipulating the tissue of a live pig is similar to that of a human, and the surgeon experiences the real sensation of operating on live tissue and blood vessels, and will confront real-tissue problems, such as associated with cauterizing vessels. There are drawbacks associated with using a live pig, however, such as anatomic limitations, the need for pre-procedure tracheostomy, anesthetic care during the procedure, and finally the ultimate disposition of the animal after finishing the surgical procedure.

Other surgical training models for simulating surgery in the throat of the human body may include the use of synthetic tissue. However, the surgeon learning the surgical skills necessary to operate in this confined area will not have the benefit of operating on real-tissue. Synthetic tissue may not have the same properties as real-tissue and may not be able to be manipulated similarly to real-tissue. For that reason, these synthetic tissue models may not provide a realistic training experience, and thus, have their limitations in surgical training.

SUMMARY

A real-tissue surgical training system may comprise a base and a harvested porcine tissue cassette, which may comprise a substrate configured to be removably mounted to the base, and harvested porcine tissue carried by the substrate and configured to simulate the oropharynx region of the human body and to receive a surgical tool therein for surgical training. The harvested porcine tissue cassette may comprise at least one simulated blood vessel associated with the harvested porcine tissue. A fluid source may be configured to simulate a heartbeat in the at least one simulated blood vessel. The harvested porcine tissue cassette may comprise at least one simulated tumor associated with the harvested porcine tissue.

The harvested porcine tissue may comprise a shortened tongue and jaws relative to natural lengths thereof. The harvested porcine tissue may also be configured to represent a larynx region of the human body. A face mask having an oral opening therein may be aligned with a corresponding oral opening of the harvested porcine tissue. The base and substrate may have corresponding alignment features to permit selective angular positioning of the harvested porcine tissue cassette relative to the base. The substrate may have a bend in a medial portion thereof. In another example, a harvested porcine tissue cassette for real-tissue surgical training may comprise a substrate configured to be removably mounted to a base and harvested porcine tissue carried by the substrate and configured to simulate the oropharynx region of the human body and to receive a surgical tool therein for surgical training.

A method aspect for making a harvested porcine tissue cassette for real-tissue surgical training may include attaching harvested porcine tissue to a substrate and configured to simulate the oropharynx region of the human body to receive a surgical tool therein for surgical training.

DESCRIPTION OF THE DRAWINGS

Other objects, features and advantages of the present invention will become apparent from the detailed description of the invention, which follows when considered in light of the accompanying drawings in which.

DETAILED DESCRIPTION

The present disclosure will now be described more fully hereinafter with reference to the accompanying drawings, in which example embodiments of the inventive concept are shown. This invention may, however, be embodied in many different forms and should not be construed as limited to the embodiments set forth herein. Rather, these embodiments are provided so that this disclosure will be thorough and complete, and will fully convey the scope of the inventive concepts to those skilled in the art. Like numbers refer to like elements throughout.

Figure 1:
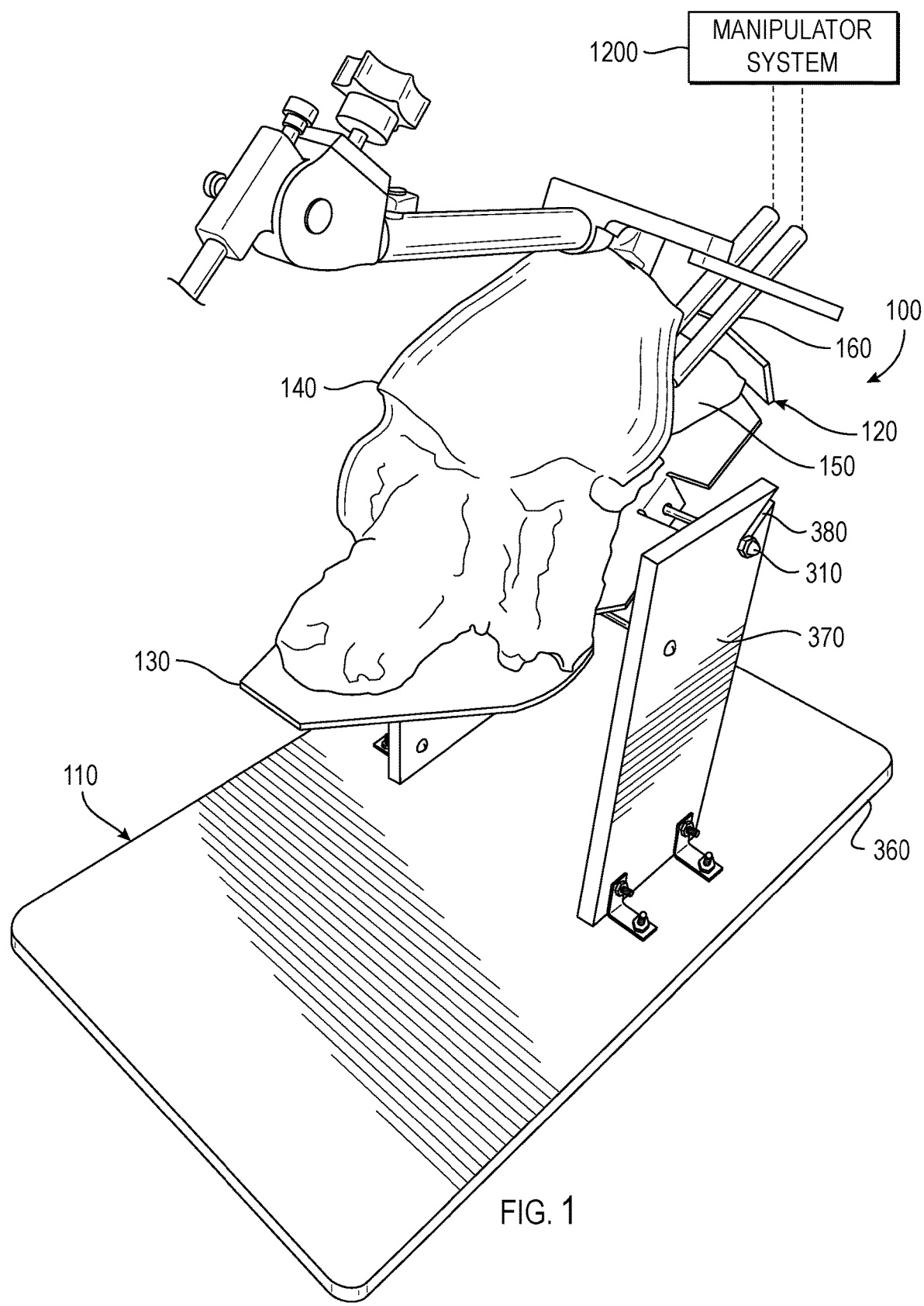
FIG. 1 is an environmental perspective view of a real-tissue surgical training system showing surgical tools inserted within an oral opening of harvested porcine tissue that is configured to simulate the oropharynx region of the human body according to an example embodiment of the disclosure.
Figure 3:
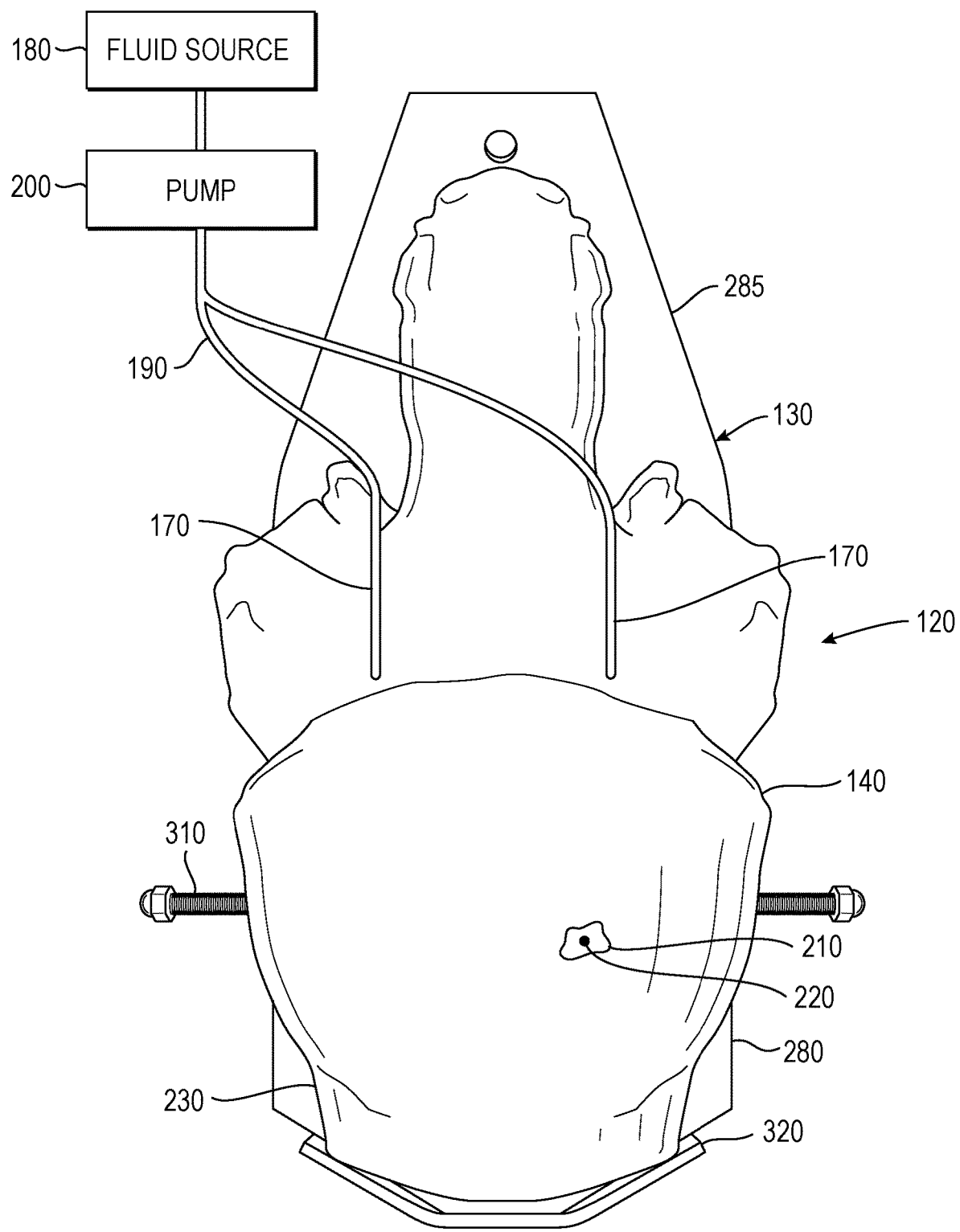
FIG. 3 is an environmental perspective view of a tissue cassette looking from the top of harvested porcine tissue carried by the substrate.
Figure 4:
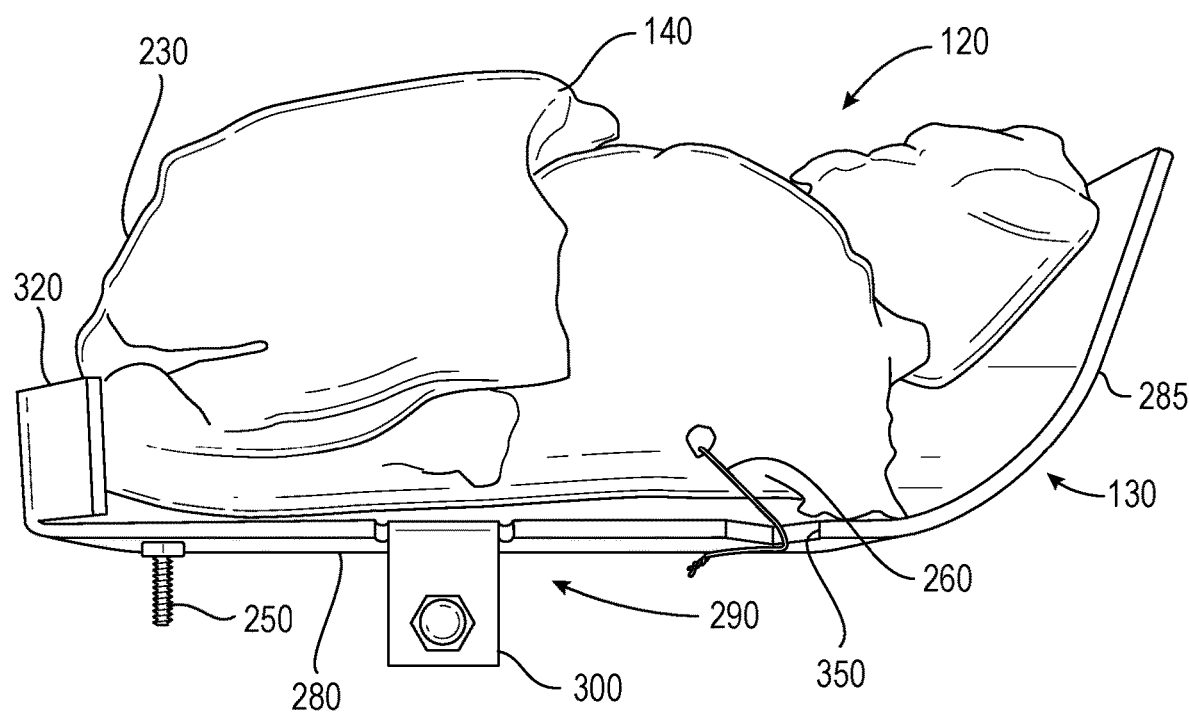
FIG. 4 is yet another environmental perspective view of a tissue cassette looking from the side of harvested porcine tissue carried by the substrate.

Referring now to FIG. 1, there is depicted at 100 a real-tissue surgical training system that includes a base 110 and a harvested porcine tissue cassette 120 that includes a substrate 130 configured to be removably mounted to the base (FIGS. 3 and 4). The tissue cassette 120 includes harvested porcine tissue 140 that is carried or supported by the substrate 130. As depicted, the harvested porcine tissue 140 is configured to represent a pharynx and larynx regions of the human body, and more particularly the oropharynx, and has an oral opening 150 that receives a surgical tool 160 for surgical training, such as part of a manipulator system 1200, e.g., a robotic surgery system and/or manual laparoscopic system as explained in greater detail with reference to FIGS. 11 and 12.

In this example, the harvested porcine tissue cassette 120 includes at least one simulated blood vessel shown by the dashed lines 170 (FIG. 3) extending through the harvested porcine tissue. A fluid source 180 containing artificial blood may be mounted adjacent to the base 110 or other support and includes a supply line 190 connected to the simulated blood vessel 170 to simulate blood flow via a fluid pump 200 and a heartbeat to artificial blood flowing in the simulated blood vessel. In this example, the simulated blood vessel 170 splits into two blood vessels as shown by the two dashed lines representative, for example, of the lingual artery and its branches, including the deep lingual artery and sublingual artery, which together arise from the external carotid artery between the superior thyroid artery and facial artery. The fluid source 180 provides a pulsating heartbeat to the artificial blood flowing through the simulated blood vessel 170. In an example that is not illustrated in detail, the fluid source 180 and pump 200 may form a closed, dead end system. A capacitance chamber may be compressed by a piston to displace fluid and impart a simulated "pulse" to the distal vascular system formed by the simulated blood vessel 170. The piston is then withdrawn and fluid that has been displaced returns to refill the capacitance chamber. The simulated blood vessel 170, fluid source 180, supply line 190, and fluid pump 200 are optional and may be omitted in some embodiments.

As shown in the breakaway section depicted at 210 in FIG. 3 corresponding to a small section of the outer surface of the harvested porcine tissue 140, at least one simulated tumor 220 may be associated with the harvested porcine tissue. For example, during the preparation of the harvested porcine tissue cassette 120, the simulated tumor 220 may be placed underneath the mucosa as part of the membrane inside the oropharynx region of the pig. An example of a simulated tumor 220 could be gel that is injected underneath the mucosa, or another gel substrate placed within an opening of the mucosa, and then closed up to be hidden from initial view and used for training. Other gels and solidifiable liquids could be injected within different sections of the oropharynx region to form a simulated tumor 220. The simulated tumor 220 is optional and may be omitted in some embodiments.

Figure 2:
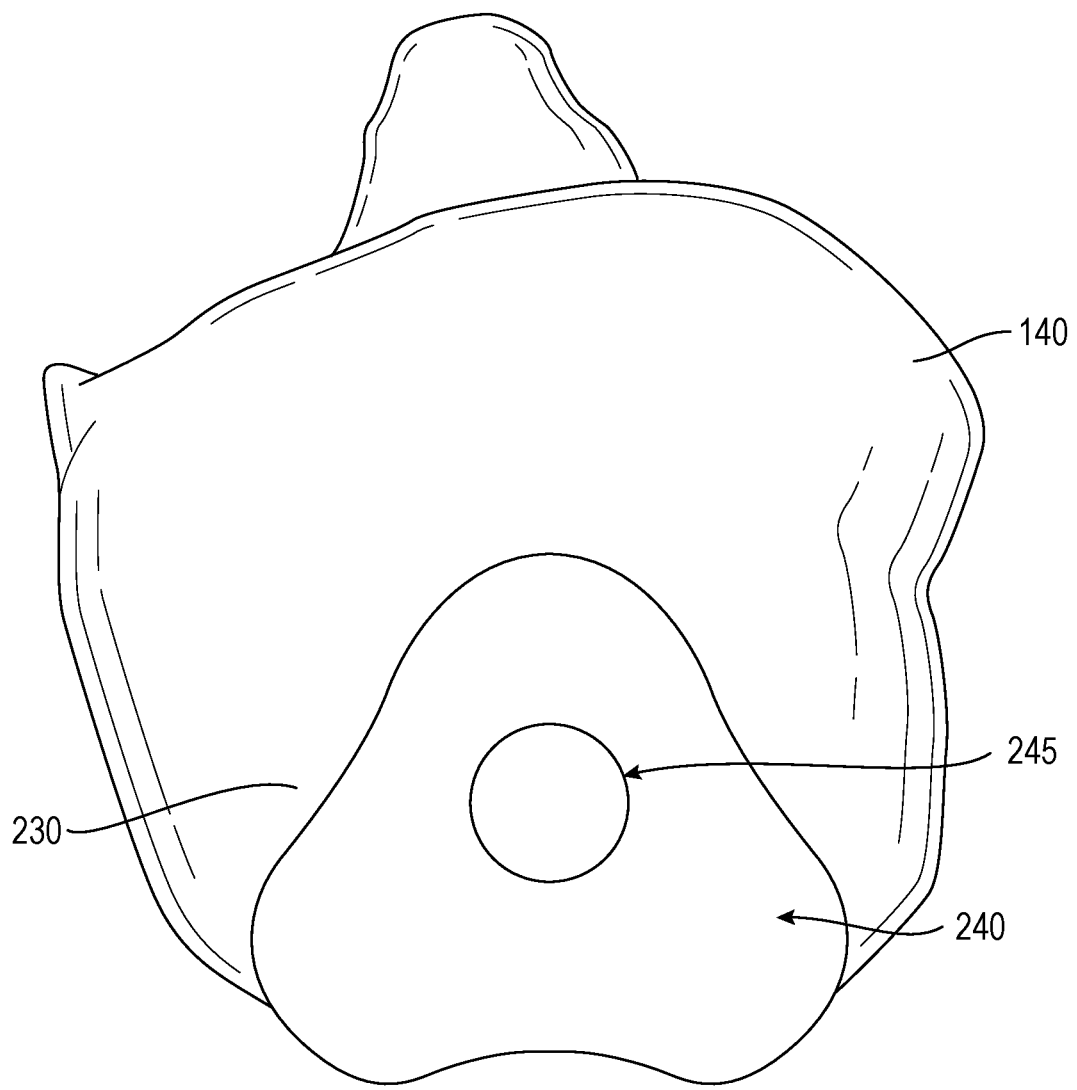
FIG. 2 is an environmental perspective view of the harvested porcine tissue showing a face mask having an opening aligned with a corresponding oral opening of the harvested porcine tissue.

As best shown in the top plan view of the harvested porcine tissue 140 in FIG. 3 and side view in FIG. 4, the harvested porcine tissue includes a shortened tongue and jaws section 230 relative to the natural lengths thereof and the tissue is configured to represent an oropharynx region of the human body. In an example depicted in FIG. 2, a face mask 240 having an oral opening 245 therein is aligned with the corresponding oral opening 150 of the harvested porcine tissue 140, such that when the oral opening is extended into its widest gap opening, the face mask permits surgical tools 160 and other surgical instruments to be inserted within the corresponding oral opening of the harvested porcine tissue. The face mask 240 may also provide a cosmetic appearance to the front or proximal section of the harvested porcine tissue having the oral opening 150. The face mask 240 could be configured as a plain cover or similar to a generic human face or other desired profile. The face mask 240 is optional and may be omitted in some embodiments.

In some embodiments, the size of the oral opening 150 may be adjusted to adjust for difficulty in training. Adjusting the size of the oral opening 150 further allows for simulating procedures of patients with different sized anatomy (e.g., people with larger versus smaller mouths, oral cavity sizes, etc.). In some embodiments, the oral opening 150 may be adjusted by wiring or clamping the jaw with an adjustable hinge to adjust the extent (e.g., angle) of the jaw opening. In further embodiments where a face mask 240 is used, the size of the opening 245 in the face mask may be adjusted. Multiple face masks 240 may be employed with different sized, fixed openings 245. In yet further embodiments, a single face mask 240 may have an adjustable size for its opening 245. For example, the face mask 240 may include one or more plates that slide into a slot in the face mask 240 to set a size of the opening 245. In some examples, the plate may have its own opening of a preset size, with different sized plates being provided to set the opening size. In further examples, the face mask 240 may have a mechanism that moves one plate with an opening relative to the face mask, for example, a rotary or linear sliding mechanism.

The harvested porcine tissue 140 that is attached to the substrate 130 to form the harvested porcine tissue cassette 120 may be prepared initially, for example, at a slaughterhouse, by amputating the head of a pig below the larynx and removing its spinal cord. Once the pig's head is amputated below the larynx, it forms a base material that may be frozen and shipped to a medical supplier or other medical provider for further processing into the harvested porcine tissue cassette 120. For example, once received at a medical supplier, the pig's head may be positioned in a head vice and the upper and lower jaws sawed off about two inches distal to the angle of the mouth of the pig. This will remove the long snout of the animal, thereby creating a system that more accurately simulates the human anatomy. The tongue may also be amputated at the same level. The cranium is sawed-off parallel to the hard palate just above the hard palate. This step removes all the neurologic tissue. The spinal cord had been previously removed when the head had been amputated at the slaughterhouse.

Figure 5:
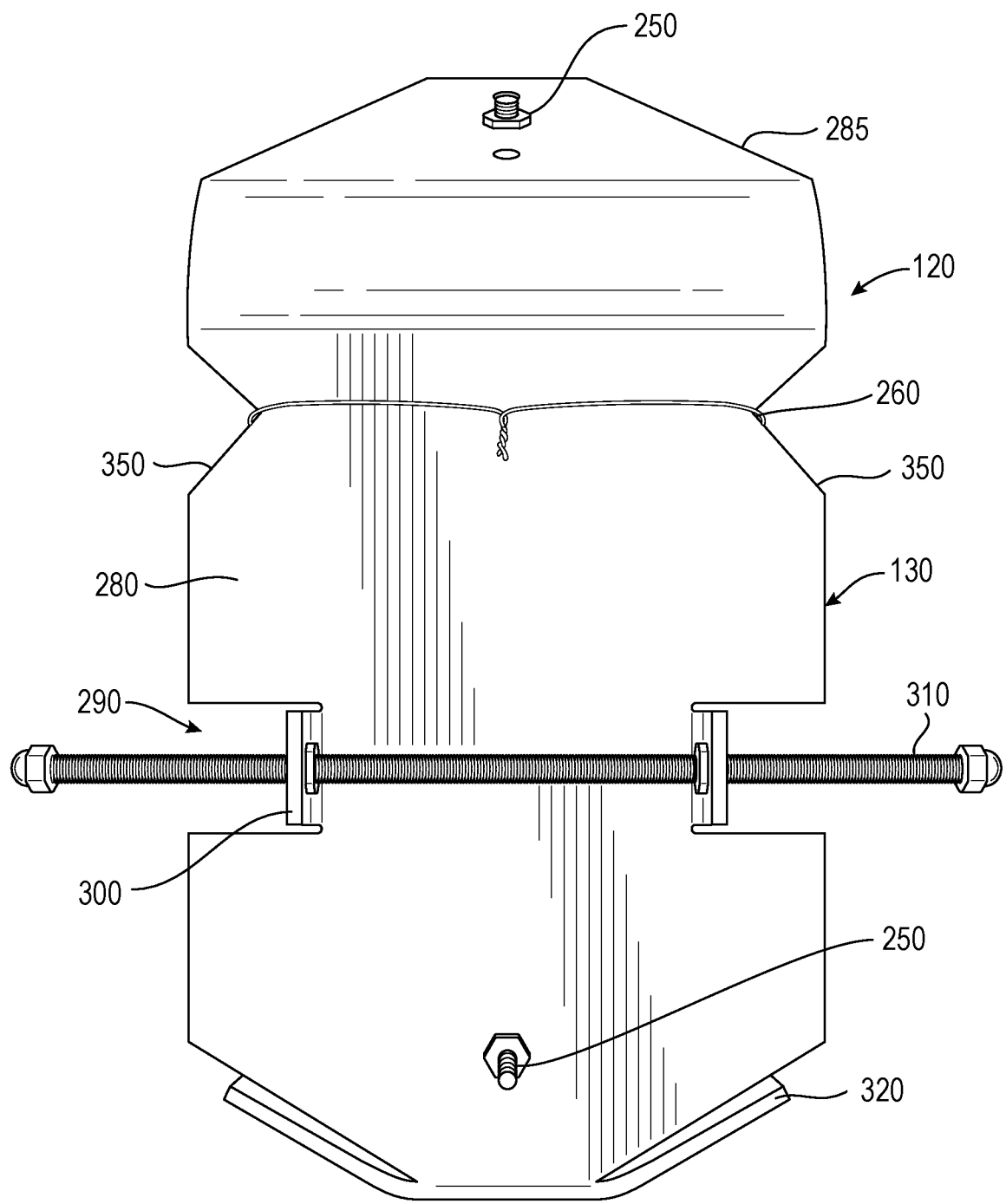
FIG. 5 is a bottom plan view of the harvested porcine tissue cassette showing the bolts and optional wire that attach the harvested porcine tissue to the substrate.
Figure 6:
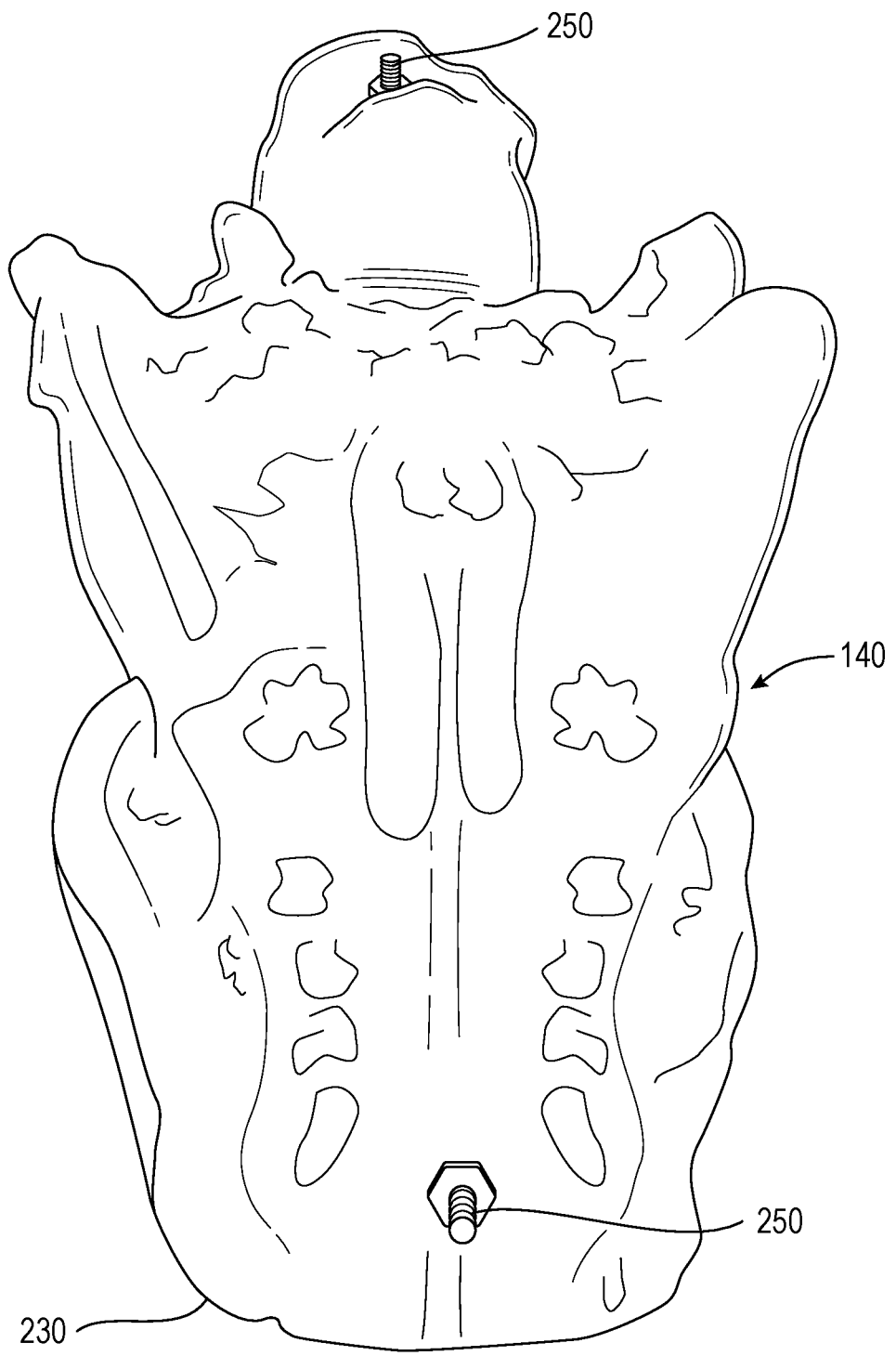
FIG. 6 is a bottom plan view of the harvested porcine tissue showing location of bolts that attach the harvested porcine tissue to the substrate.

The soft tissue surrounding the larynx is removed, and the muscle lateral to the mandible is removed, which facilitates mobility of the jaw. A hole is drilled in the hard palate and within the posterior aspect of the distal larynx, which becomes points of attachment of the harvested porcine tissue 140 to the substrate 130 by receiving bolts 250 that attach to the substrate (FIGS. 5 and 6). In some embodiments, optionally, holes may be drilled in both mandibular plates, and the harvested porcine tissue 140 via its mandibular plates may be further attached to the substrate 130 using wire 260 (FIG. 5) to suspend the harvested porcine tissue. The holes and wire 260 are optional and may be omitted in some embodiments. The bolts 250 that extend through the holes drilled in the hard palate and both mandibular plates are shown in the example of the bottom plan view of the substrate 130 in FIG. 5, and help secure the harvested porcine tissue 140 to the substrate 130. In FIG. 6, the substrate 130 has been removed from the harvested porcine tissue 140 to show the positioning of the bolts 250 relative to the harvested porcine tissue.

Figure 7:
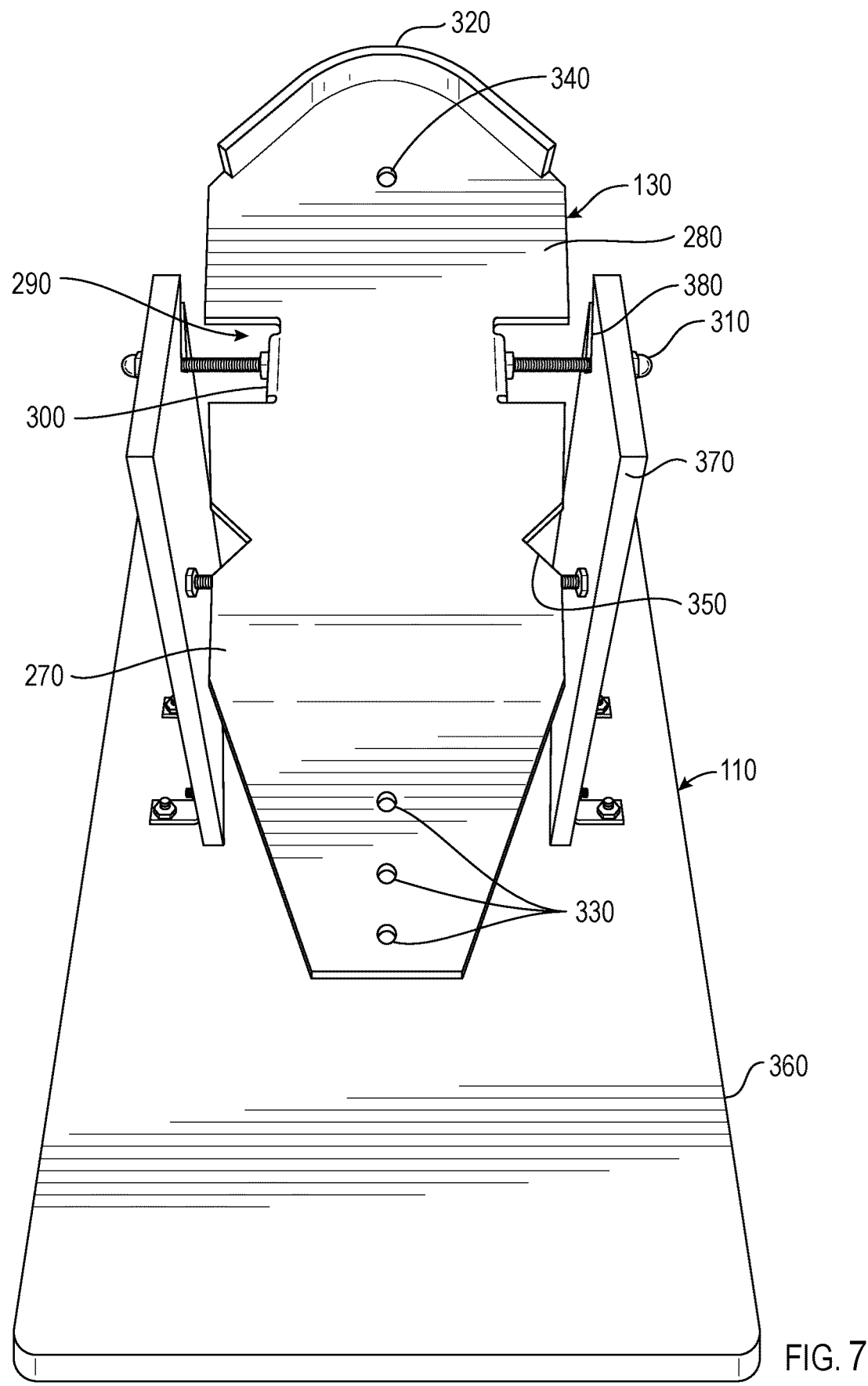
FIG. 7 is an isometric view of the substrate removably mounted to the base.
Figure 8:
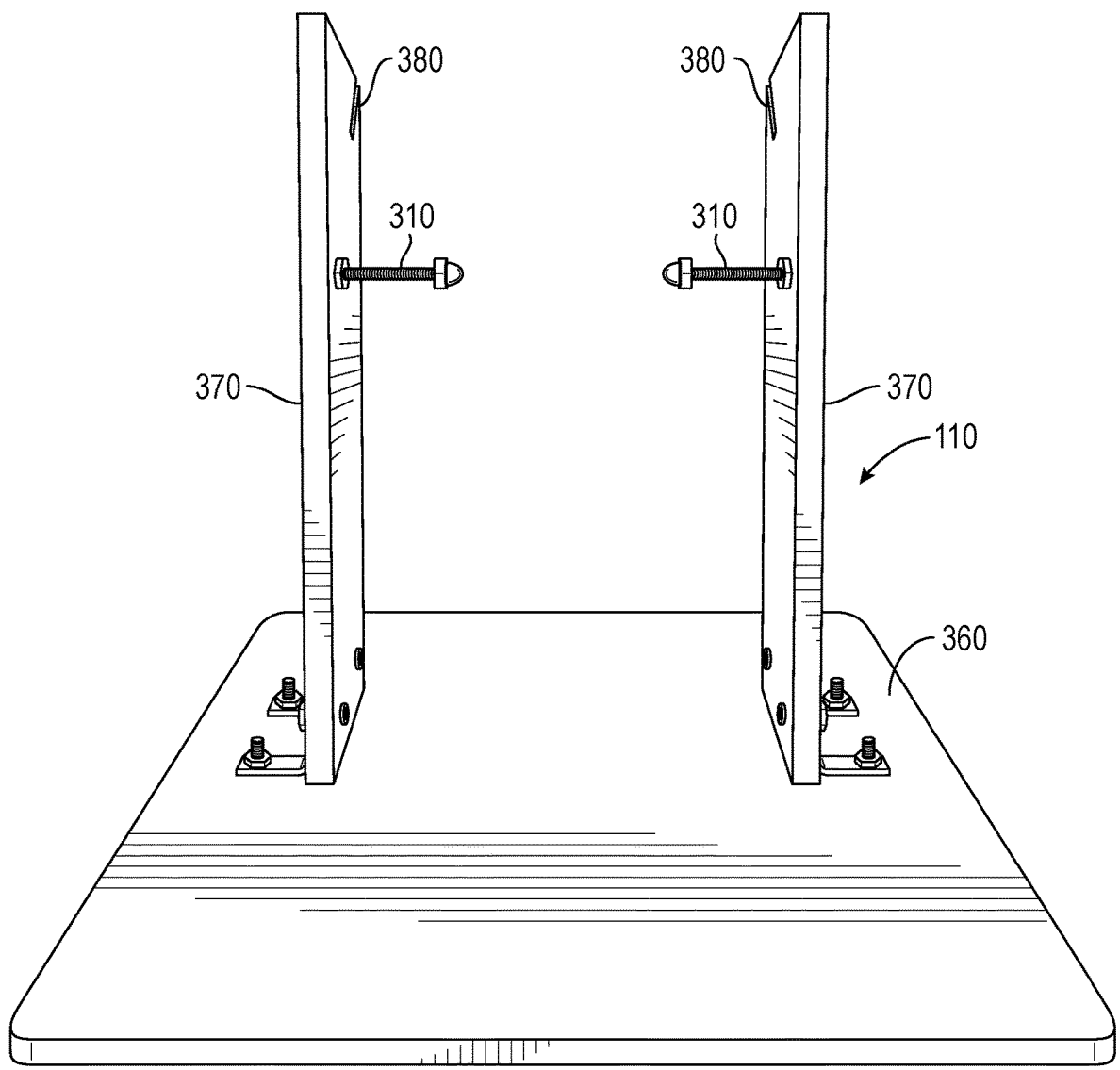
FIG. 8 is an isometric view of the base.
Figure 9:
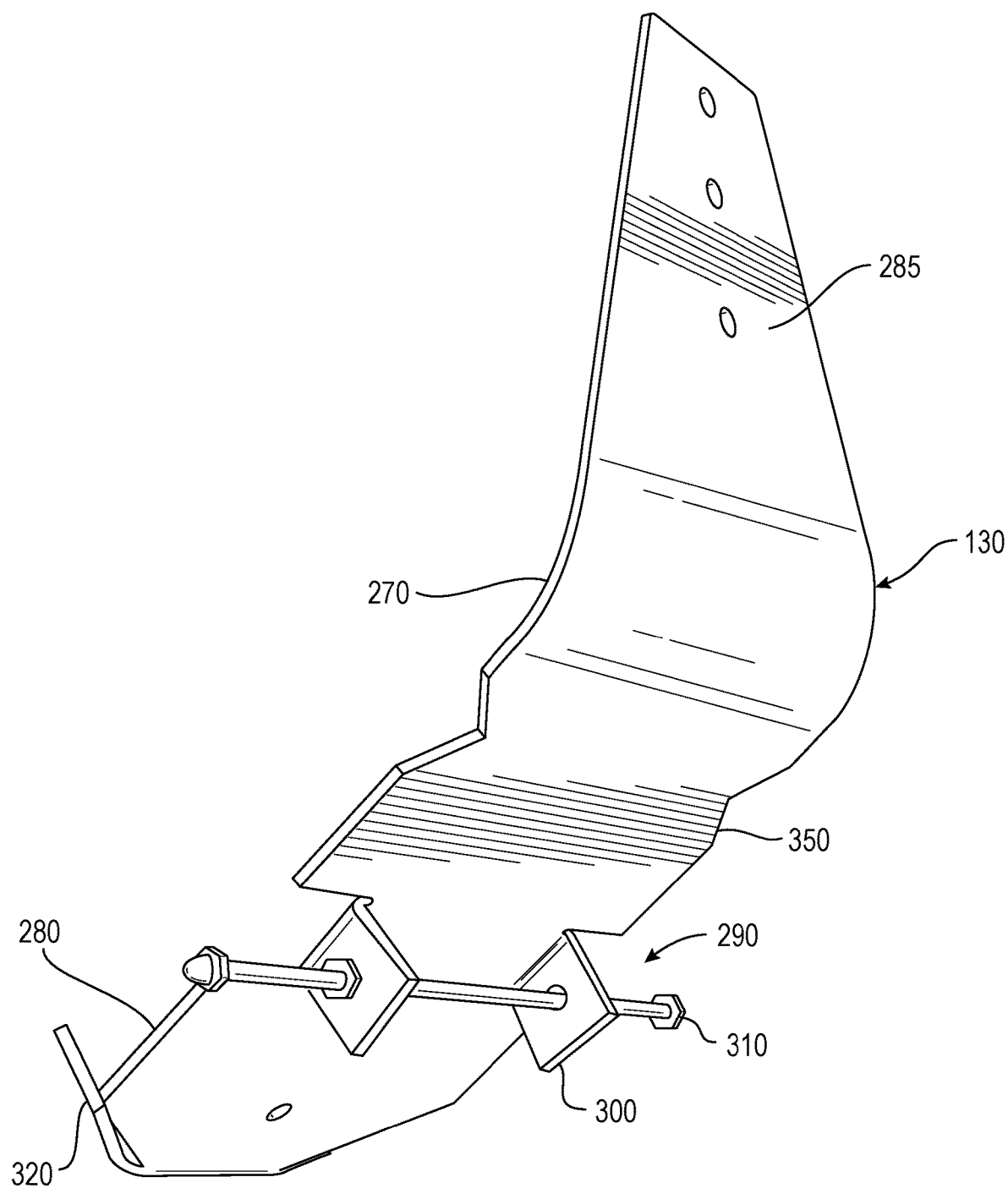
FIG. 9 is an isometric view of the substrate that may be removably mounted to the base.

Referring now to FIGS. 7-9, greater details of the base 110 and the substrate 130 that is configured to be removably mounted to the base are depicted. The substrate 130 is shown removably mounted on the base 110 (FIG. 7) and without the harvested porcine tissue 140. The base 110 is illustrated in FIG. 8 and the substrate 130 is depicted in FIG. 9.

The substrate 130 may be formed from a metal material such as lightweight aluminum, or preferably from a lightweight plastic material, such as a thermoplastic acrylic-polyvinylchloride material, e.g., Kydex. In an example, the substrate 130 is formed as a plate that is about 5.5 inches by 14 inches, however, the disclosure is not limited thereto or thereby and other sizes may be used. The substrate 130 includes a bend 270 in a medial portion thereof as best shown in FIG. 9, showing the bend to be about 30 degrees+/−10 degrees from the horizontal or planar portion 280 of the substrate. An inclined section 285 extending from the bend 270 forms a distal section of the substrate that receives an end of the harvested porcine tissue 140 opposite the oral opening 150. A hinge mounting mechanism 290 is formed by cutting two parallel lines at left and right side edges of a horizontal or planar portion 280 of the substrate 130, and the ends between the cut lines bent at 90° to form mounting tabs 300. Holes are drilled in the mounting tabs 300 and a mounting rod 310 received through the holes in the mounting tabs (FIG. 9).

A three-quarter inch front bumper 320 is bent at 90° to the plane at the end of the horizontal portion 280 of the substrate 130 opposite the inclined section 285. The proximal end of the harvested porcine tissue 140 that has the oral opening 150 abuts against that front bumper 320 to retain and help secure the simulated oropharynx region against the front bumper, as best shown in FIGS. 3-4. Three holes 330 are drilled in the inclined section 285 of the substrate 130, and a single hole 340 is drilled in the horizontal portion 280 of the substrate 130 adjacent to the front bumper 320 (FIG. 7). These holes 330, 340 permit the bolts 250 to be inserted through the hard palate and mandibular plates of the harvested porcine tissue 140 to secure the harvested porcine tissue to the substrate 130 as shown in FIG. 5. The wire 260 may be used to help retain the harvested porcine tissue 140 on the substrate 130, where the wire if it is used engages "V" cuts 350 formed in the side of the substrate as best shown in FIG. 7, showing the V cuts formed at each side of the substrate. The wire 260 and V cuts 350 are optional and may be omitted in some embodiments.

The base 110 is formed as a support stand and supports the harvested porcine tissue cassette 120, and includes a large rectangular configured support plate 360, which in an example, is formed from polyvinylchloride (PVC), and having two vertical and parallel support legs 370 formed in this example as rectangular configured PVC plates attached at right angles to the larger support plate 360 (FIGS. 7 and 8). In an example, the vertical support legs 370 may each be about four inches in height and may be placed about six inches apart. Each vertical support leg includes an angled slot 380 extending into the respective support leg near an upper edge and extends downward about an inch. Each slot 380 receives the mounting rod 310 of the tissue cassette 120 allowing the substrate to be removably mounted to the base 110 by sliding the mounting rod 310 into the slots 380. In this example, the harvested porcine tissue cassette 120 may be removed from a freezer located at a surgical training facility or medical school classroom, unthawed, and then inserted onto the base 110 by sliding the mounting rods 310 into the angled slots 380 cut within each vertical support leg 370.

The base 110 and substrate 130 have corresponding alignment features to permit selective angular positioning of the harvested porcine tissue cassette 120 relative to the base. For example, the vertical support legs 370 may each include a plurality of holes that are positioned and configured to receive an alignment rod 390 therein (FIG. 8), such that when the substrate 130 is received onto the base 110, the alignment rods are positioned in selected holes to permit the selective angular positioning of the harvested porcine tissue cassette 120 relative to the base to facilitate surgical training in a natural position related to oropharyngeal surgery. Additionally or alternatively, in some embodiments, the support plate 360 may have a vertically extending member configured to support a distal portion of the substrate 130. The vertically extending member may have a height adjustment feature (e.g., via a telescoping member, an adjustable track, or the like). Additionally or alternatively, the vertical support legs 370 may have a plurality of angled slots 380 in each leg 370, which may allow for further adjustment of the angular position of the tissue cassette 120. Various ones of the angled slots 380 may have different inclination angles with respect to each other.

For surgical training, an F-K retractor may be placed within the oral opening 150 of the harvested porcine tissue 140 and any surgical tools and instruments, such as employed with a robot or manual laparoscopic system positioned within the oral opening 150 for surgical training. Other retractor devices may possibly be used, including a Lars retractor or similar retractor devices. Once the surgical training on the mounted harvested porcine tissue cassette 120 is completed, the harvested porcine tissue cassette may be removed from the base 110 and discarded, and a substitute harvested porcine tissue cassette mounted to the base for further surgical training.

Figure 10:
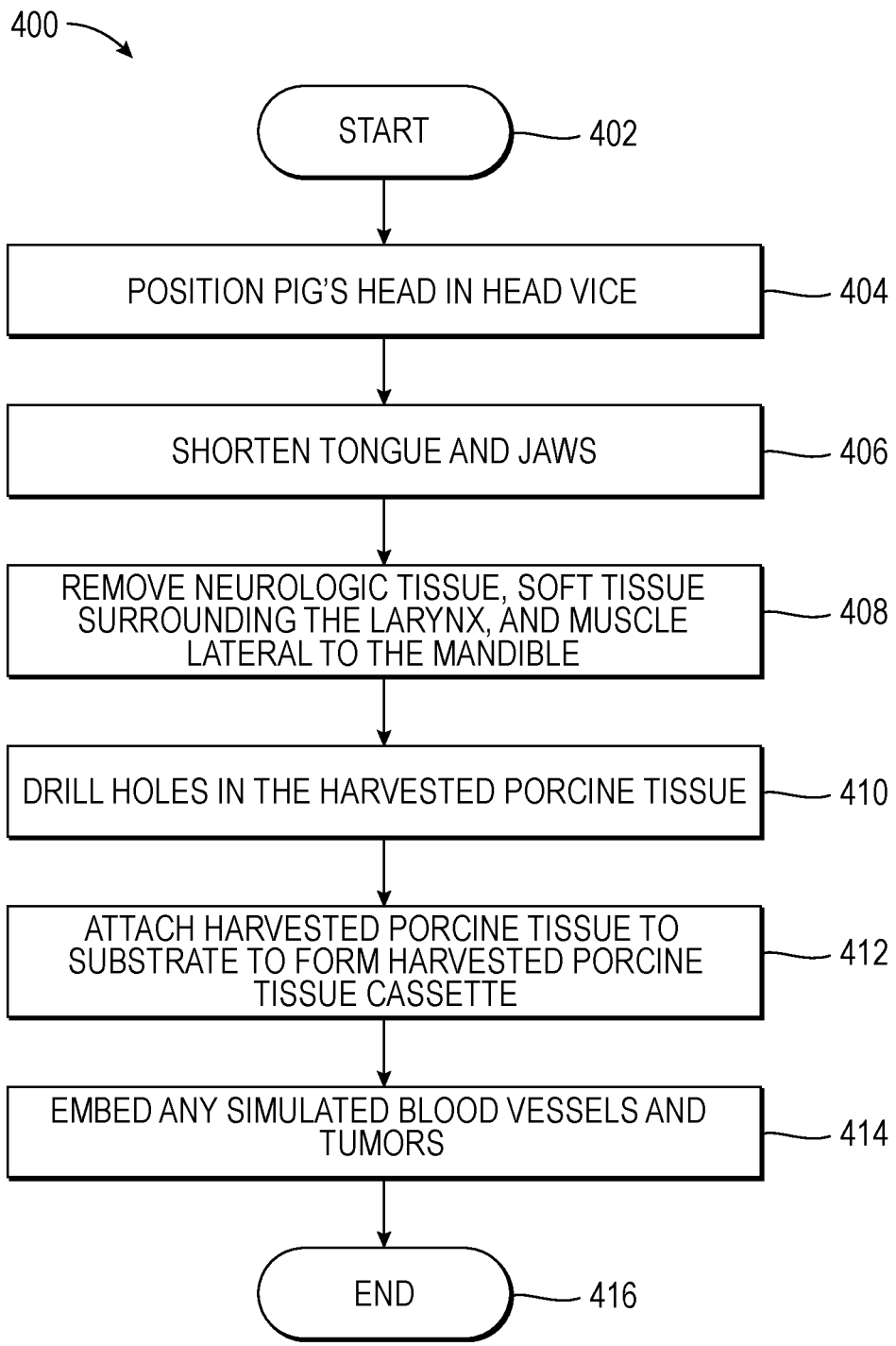
FIG. 10 is a flowchart showing a method for making the harvested porcine tissue cassette.

Referring now to FIG. 10, there is illustrated generally at 400 a high-level flowchart showing a method of manufacturing a harvested porcine tissue cassette 120 for the real-tissue surgical training. The process starts (Block 402) and the pig's head is positioned in a head vice (Block 404). At the slaughterhouse or other appropriate location, the pig's head had been amputated and its spinal cord removed. The tongue and jaws are shortened relative to the natural lengths thereof by cutting the tongue and upper and lower jaws (Block 406). The neurologic tissue, spinal cord, soft tissue surrounding the larynx, and the muscle lateral to the mandible are removed (Block 408). The holes are drilled in the harvested porcine tissue (Block 410). The harvested porcine tissue is attached to the substrate via the bolts 250 and wire 260 (Block 412). Optionally, simulated blood vessels 170 and tumors 220 are embedded (Block 414) and the process ends (Block 416).

Further steps at the time of surgical training may include removably mounting the harvested porcine tissue cassette 120 to the base 110 and optionally connecting the fluid source 180 to the simulated blood vessels 170 to begin surgical training. Different surgical tools may be inserted within the oral opening 150 of the harvested porcine tissue 140, such as cauterizing tools, scissors, cameras, and other surgical tools commonly associated with surgically operating in the oropharynx region of the human body.

The real-tissue surgical training system 100 may be used, for example, with remotely operated, computer-assisted or teleoperated surgical systems, such as those described in, for example, U.S. Pat. No. 9,358,074 (filed May 31, 2013) to Schena et al., entitled "Multi-Port Surgical Robotic System Architecture", U.S. Pat. No. 9,295,524 (filed May 31, 2013) to Schena et al., entitled "Redundant Axis and Degree of Freedom for Hardware-Constrained Remote Center Robotic Manipulator", and U.S. Pat. No. 8,852,208 (filed Aug. 12, 2010) to Gomez et al., entitled "Surgical System Instrument Mounting", each of which is hereby incorporated by reference in its entirety. Further, the real-tissue surgical trailing system 100 described herein may be used, for example, with a da Vinci® Surgical System, such as the da Vinci X® Surgical System or the da Vinci Xi® Surgical System, both with or without Single-Site® single orifice surgery technology, all commercialized by Intuitive Surgical, Inc., of Sunnyvale, California. Although various embodiments described herein are discussed in connection with a manipulating system of a teleoperated surgical system, the present disclosure is not limited to use with a teleoperated surgical system. Various embodiments described herein can optionally be used in conjunction with hand held instruments, such as laparoscopic tools for real-time surgical training with a harvested porcine tissue cassette.

Figure 11:
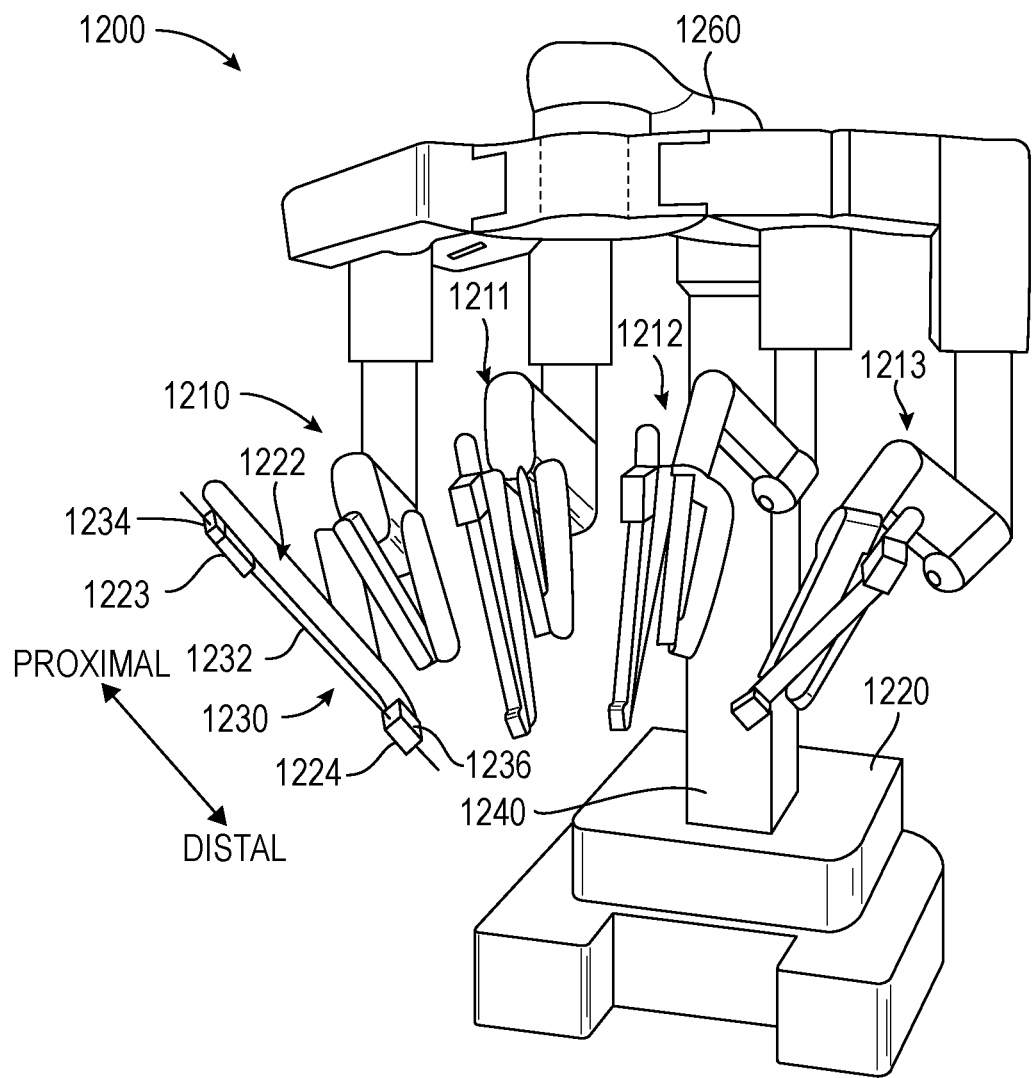
FIG. 11 is a perspective view of a manipulator system according to an example embodiment of the disclosure.

As discussed above, in accordance with various embodiments, surgical tools or instruments of the present disclosure are configured for use in teleoperated, computer-assisted surgical systems employing robotic technology (sometimes referred to as robotic surgical systems). Referring now to FIG. 11, an embodiment of a manipulator system 1200 of a computer-assisted surgical system, to which surgical instruments are configured to be mounted for use, is shown. Such a surgical system may further include a user control system, such as a surgeon console (not shown) for receiving input from a user to control instruments coupled to the manipulator system 1200, as well as an auxiliary system, such as auxiliary systems associated with the DA VINCI X® and DA VINCI XI®, Da Vinci SP.

As shown in the embodiment of FIG. 11, a manipulator system 1200 includes a base 1220, a main column 1240, and a main boom 1260 connected to main column 1240. Manipulator system 1200 also includes a plurality of manipulator arms 1210, 1211, 1212, 1213, which are each connected to main boom 1260. Manipulator arms 1210, 1211, 1212, 1213 each include an instrument mount portion 1222 to which an instrument 1230 may be mounted, which is illustrated as being attached to manipulator arm 1210.

Instrument mount portion 1222 may include a drive assembly 1223 and a cannula mount 1224, with a transmission mechanism 1234 of the instrument 1230 connecting with the drive assembly 1223, according to an embodiment. Cannula mount 1224 is configured to hold a cannula 1236 through which a shaft 1232 of instrument 1230 may extend to a surgery site during a surgical procedure. Drive assembly 1223 contains a variety of drive and other mechanisms that are controlled to respond to input commands at the surgeon console and transmit forces to the transmission mechanism 1234 to actuate the instrument 1230. Although the embodiment of FIG. 11 shows an instrument 1230 attached to only manipulator arm 1210 for ease of viewing, an instrument may be attached to any and each of manipulator arms 1210, 1211, 1212, 1213.

Figure 12:
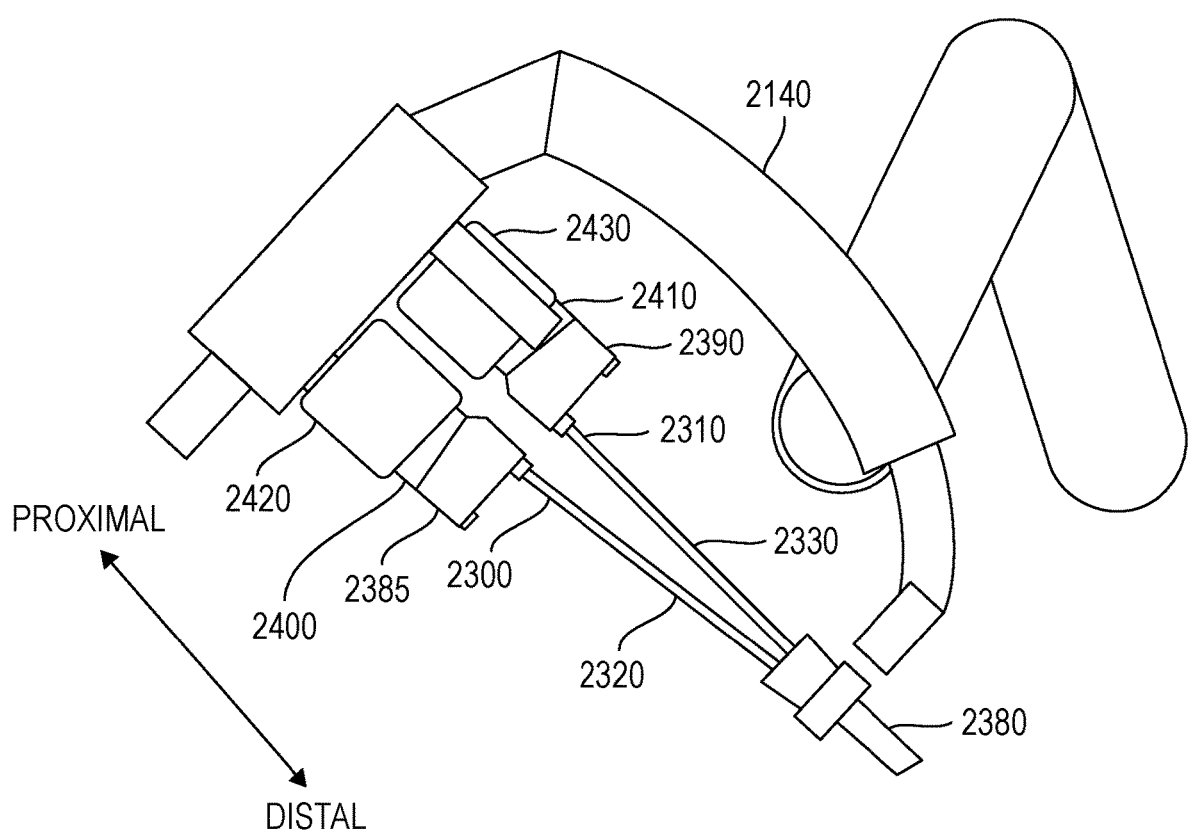
FIG. 12 is a partial schematic view of an embodiment of a manipulator system having a manipulator arm with two instruments in an installed position according to the present disclosure.

Other configurations of surgical systems, such as surgical systems configured for single-port surgery, are also contemplated. For example, with reference now to FIG. 12, a portion of an embodiment of a manipulator arm 2140 of a manipulator system with two surgical instruments 2300, 2310 in an installed position is shown. The surgical instruments 2300, 2310 can generally correspond to different instruments used for real-time tissue training using the harvested porcine tissue cassette. For example, the embodiments described herein may be used with a DA VINCI SP® Surgical System, commercialized by Intuitive Surgical, Inc. of Sunnyvale, California. The schematic illustration of FIG. 12 depicts only two surgical instruments for simplicity, but more than two surgical instruments may be mounted in an installed position at a manipulator system as those having ordinary skill in the art are familiar. Each surgical instrument 2300, 2310 includes a shaft 2320, 2330 having at a distal end a moveable end effector or an endoscope, camera, or other sensing device, and may or may not include a wrist mechanism (not shown) to control the movement of the distal end.

In the embodiment of FIG. 12, the distal end portions of the surgical instruments 2300, 2310 are received through a single port structure 2380 to be introduced into the harvested porcine tissue through the opening of the mouth and associated upper and lower jaws and into communication with the oropharynx region. As shown, the port structure includes a cannula and an instrument entry guide inserted into the cannula. Individual instruments are inserted into the entry guide to reach a surgical site corresponding to the oropharynx region of the porcine tissue that simulates the oropharynx region of the human body.

Other configurations of manipulator systems that can be used in conjunction with the present disclosure can use several individual manipulator arms. In addition, individual manipulator arms may include a single instrument or a plurality of instruments. Further, as discussed above, an instrument may be a surgical instrument with an end effector or may be a camera instrument or other sensing instrument utilized during a surgical procedure to provide information, (e.g., visualization, electrophysiological activity, pressure, fluid flow, and/or other sensed data) of a remote surgical site.

Transmission mechanisms 2385, 2390 are disposed at a proximal end of each shaft 2320, 2330 and connect through a sterile adaptor 2400, 2410 with drive assemblies 2420, 2430, which contain a variety of internal mechanisms (not shown) that are controlled by a controller (e.g., at a control cart of a surgical system) to respond to input commands at a surgeon side console of a surgical system to transmit forces to the force transmission mechanisms 2385, 2390 to actuate surgical instruments 2300, 2310.

The embodiments described herein are not limited to the embodiments of FIG. 11 and FIG. 12, and various other teleoperated, computer-assisted surgical system configurations may be used with the embodiments described herein. The diameter or diameters of an instrument shaft and end effector are generally selected according to the size of the cannula with which the instrument will be used and depending on the surgical procedures being performed.

This description and the accompanying drawings that illustrate various embodiments should not be taken as limiting. Various mechanical, compositional, structural, electrical, and operational changes may be made without departing from the scope of this description and the invention as claimed, including equivalents. In some instances, well-known structures and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to another embodiment, the element may nevertheless be claimed as included in the other embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the example term "below" can encompass both positions and orientations of above and below. A device may be otherwise oriented (rotated 90 degrees or at other orientations) and the spatially relative descriptors used herein interpreted accordingly.

Further modifications and alternative embodiments will be apparent to those of ordinary skill in the art in view of the disclosure herein. For example, the devices and methods may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as examples. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the spirit and scope of the present teachings and following claims.

It is to be understood that the particular examples and embodiments set forth herein are non-limiting, and modifications to structure, dimensions, materials, and methodologies may be made without departing from the scope of the present teachings.

Many modifications and other embodiments of the invention will come to the mind of one skilled in the art having the benefit of the teachings presented in the foregoing descriptions and the associated drawings. Therefore, it is to be understood that the invention is not to be limited to the specific embodiments disclosed, and that the modifications and embodiments are intended to be included within the scope of the dependent claims.

The invention claimed is:

1. A real-tissue surgical training system comprising:
a base; and
a harvested porcine tissue cassette comprising
a substrate configured to be removably mounted to the base, and
harvested porcine tissue carried by the substrate and configured to simulate the oropharynx region of the human body and to receive a surgical tool therein for surgical training, the harvested porcine tissue comprising a shortened tongue and shortened jaws relative to natural lengths thereof.

2. The system of claim 1, wherein the harvested porcine tissue cassette comprises at least one simulated blood vessel associated with the harvested porcine tissue.

3. The system of claim 2, further comprising a fluid source configured to simulate a heartbeat in the at least one simulated blood vessel.

4. The system of claim 1, wherein the harvested porcine tissue cassette comprises at least one simulated tumor associated with the harvested porcine tissue.

5. The system of claim 1, wherein the harvested porcine tissue is also configured to represent a larynx region of the human body.

6. The system of claim 1, further comprising a face mask having an oral opening therein aligned with a corresponding oral opening of the harvested porcine tissue.

7. The system of claim 1, wherein the base and substrate have corresponding alignment features to permit selective angular positioning of the harvested porcine tissue cassette relative to the base.

8. The system of claim 1, wherein the substrate has a bend in a medial portion thereof.

9. A harvested porcine tissue cassette for real-tissue surgical training comprising:
a substrate configured to be removably mounted to a base; and
harvested porcine tissue carried by the substrate and configured to simulate the oropharynx region of the human body and to receive a surgical tool therein for surgical training, the harvested porcine tissue comprising a shortened tongue and shortened jaws relative to natural lengths thereof.

10. The harvested porcine tissue cassette of claim 9, further comprising at least one simulated blood vessel associated with the harvested porcine tissue.

11. The harvested porcine tissue cassette of claim 9, further comprising at least one simulated tumor associated with the harvested porcine tissue.

12. The harvested porcine tissue cassette of claim 9, wherein the harvested porcine tissue is also configured to represent a larynx region of the human body.

13. The harvested porcine tissue cassette of claim 9, wherein the substrate has a bend in a medial portion thereof.

14. A method for making a harvested porcine tissue cassette for real-tissue surgical training comprising:
shortening a tongue and shortening jaws of harvested porcine tissue relative to natural lengths thereof; and
attaching the shortened tongue and shortened jaws of the harvested porcine tissue to a substrate and configured to simulate the oropharynx region of the human body and to receive a surgical tool therein for surgical training.

15. The method of claim 14, further comprising embedding at least one simulated blood vessel within the harvested porcine tissue.

16. The method of claim 14, further comprising embedding at least one simulated tumor within the harvested porcine tissue.

17. The method of claim 14, wherein the harvested porcine tissue is also configured to represent a larynx region of the human body.

18. The method of claim 14, wherein the substrate has a bend in a medial portion thereof.

19. A harvested porcine tissue cassette for real-tissue surgical training comprising:
a substrate configured to be removably mounted to a base;
harvested porcine tissue carried by the substrate and configured to simulate the oropharynx region of the human body and to receive a surgical tool therein for surgical training; and
a face mask having an oral opening therein aligned with a corresponding oral opening of the harvested porcine tissue.

20. The harvested porcine tissue cassette of claim 19, further comprising at least one simulated blood vessel associated with the harvested porcine tissue.

21. The harvested porcine tissue cassette of claim 19, further comprising at least one simulated tumor associated with the harvested porcine tissue.

* * * * *